United States Patent
Kirwan, Jr. et al.

(10) Patent No.: US 6,749,610 B2
(45) Date of Patent: Jun. 15, 2004

(54) ELECTRO-SURGICAL FORCEPS HAVING FULLY PLATED TINES AND PROCESS FOR MANUFACTURING SAME

(75) Inventors: Lawrence T. Kirwan, Jr., Pembroke, MA (US); John Paul Ariola, Jr., Norton, MA (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 161 days.

(21) Appl. No.: 10/219,104

(22) Filed: Aug. 15, 2002

(65) Prior Publication Data

US 2004/0034349 A1 Feb. 19, 2004

(51) Int. Cl.$^7$ ............................................ A61B 18/14
(52) U.S. Cl. ........................ 606/51; 606/52; 29/825
(58) Field of Search ........................ 606/45, 48–52; 29/825

(56) References Cited

U.S. PATENT DOCUMENTS

| | | | |
|---|---|---|---|
| 3,685,518 A | 8/1972 | Beuerle et al. | 128/303.17 |
| 4,492,231 A | 1/1985 | Auth | 128/303.17 |
| 5,196,009 A | 3/1993 | Kirwan, Jr. | 606/51 |
| 5,324,289 A | 6/1994 | Eggers | 606/48 |
| 5,603,711 A | 2/1997 | Parins et al. | 606/51 |
| 5,693,052 A | 12/1997 | Weaver | 606/51 |
| 5,700,261 A | 12/1997 | Brinkerhoff | 606/41 |
| 5,743,906 A | 4/1998 | Parins et al. | 606/51 |
| 5,776,128 A | 7/1998 | Eggers | 606/48 |
| 5,810,808 A | 9/1998 | Eggers | 606/48 |
| 5,925,045 A | 7/1999 | Reimels et al. | 606/48 |
| 5,947,964 A | 9/1999 | Eggers et al. | 606/41 |
| 6,059,783 A | 5/2000 | Kirwan, Jr. | 606/51 |
| 6,283,987 B1 | 9/2001 | Laird et al. | 607/96 |
| 6,293,946 B1 | 9/2001 | Thorne | 606/48 |
| 6,296,637 B1 | 10/2001 | Thorne et al. | 606/41 |
| 6,298,550 B1 | 10/2001 | Kirwan, Jr. | 29/825 |
| 6,312,428 B1 | 11/2001 | Eggers et al. | 606/41 |
| 6,358,273 B1 | 3/2002 | Strul et al. | 607/96 |

*Primary Examiner*—Lee Cohen
(74) *Attorney, Agent, or Firm*—Weingarten, Schurgin, Gagnebin & Lebovici LLP

(57) ABSTRACT

An electro-surgical forceps has a pair of tines. At least one of the tines has an inner core of a metal such as stainless steel, nickel, or titanium, and an outer plating of a material having a thermal conductivity and preferably also an electrical conductivity greater than the core material. The outer plating covers all or substantially all of the tine. The outer plating is suitably formed by an electroplating process.

14 Claims, 4 Drawing Sheets

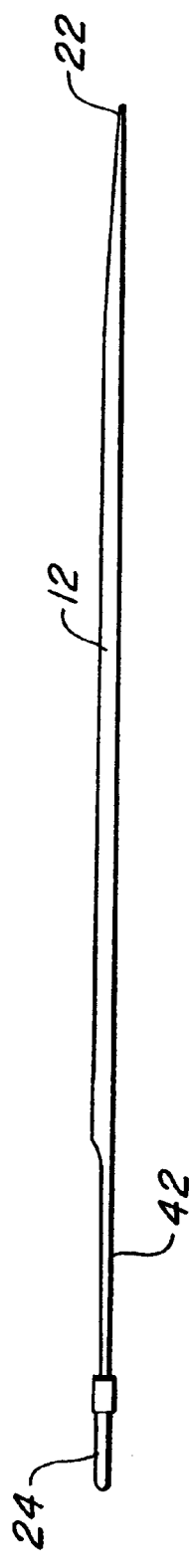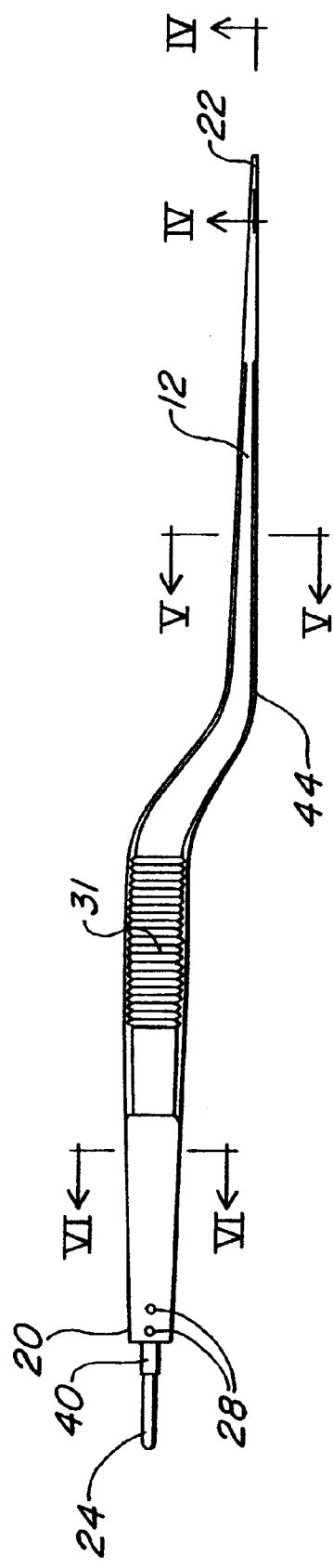

ELECTRO-SURGICAL FORCEPS HAVING FULLY PLATED TINES AND PROCESS FOR MANUFACTURING SAME

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

Electro-surgical forceps have a pair of resilient blades or arms that are used for grasping and coagulating tissue. The forceps may be monopolar or bipolar. In monopolar forceps, the blades are welded or otherwise joined to form an electrode in electrical communication with an electrical generator. Current flows from the active electrode through the patient's tissue to a dispersive electrode in contact with the patient's skin (which may be at some distance from the forceps) and back to the generator. In bipolar forceps, each blade of the pair comprises an electrode in communication with an electrical generator. Current flows from one blade through the tissue to the other blade.

In some instances, tissue may adhere or stick to the tips of the blades. If sticking occurs, the surgeon must pull on the forceps to release it from the tissue, possibly causing further bleeding and requiring that the forceps be cleaned. It is known to prevent or minimize such sticking of tissue to electrosurgical forceps by manufacturing the blades of the forceps from nickel. See, for example, U.S. Pat. No. 5,196,009. During high power operation, some eschar buildup and some sticking of the tissue to the tips still may occur.

Another known manner of preventing or minimizing sticking is to form the blades from a metal or metal alloy having a relatively high thermal conductivity, such as copper, that is able to transfer heat away from the tips of the blades. By keeping the tissue cooler, for example, below the boiling point of water, coagulation is able to occur without sticking of the tissue. See, for example, U.S. Pat. No. 4,492,231. Nickel is more biocompatible with human tissue than copper and is preferable for contact with tissue, as well as providing additional non-stick capabilities. Thus another known forceps provides blades formed of an inner layer of copper or copper alloy having a thickness sufficient to dissipate heat and an outer covering of a strong, biocompatible metal or metal alloy such as nickel metallurgically bonded to the copper layer. See U.S. Pat. Nos. 6,059,783 and 6,298,550, the disclosures of which are incorporated by reference herein.

SUMMARY OF THE INVENTION

The present invention provides an electro-surgical forceps having an outer plating covering the entire surface of the tines, from the tip to the cap. The plating material has a greater thermal conductivity and preferably also a greater electrical conductivity than the core material of the tines. In this manner, a thinner plating can be used than in prior art forceps that are plated only at the tips while still achieving sufficient heat reduction to prevent or minimize sticking of the tissue and eschar buildup.

More particularly, the forceps has a pair of tines, each tine being generally elongated and having a tip and an opposite end fixed within an insulating cap portion. At least one of the tines is electrically connected to at least one terminal within the cap portion. The tine is formed of a core comprising a metal layer formed of stainless steel, nickel or titanium. An outer plating covers the entire surface of the core. The outer plating is formed of a material having a thermal conductivity or an electrical conductivity greater than the core. Suitable outer plating materials include commercially pure silver, rhodium, gold, aluminum, palladium, tungsten, or nickel.

The plating thickness should be at least 0.001 inch to provide sufficient heat and/or electrical conductivity and wear resistance. The thickness should be no greater than 0.010 inch to minimize the amount of plating material needed. A suitable range of plating thickness is 0.004 inch to 0.008 inch. The plating is preferably formed by an electroplating process, although other plating processes may be used.

DESCRIPTION OF THE DRAWINGS

The invention will be more fully understood from the following detailed description taken in conjunction with the accompanying drawings in which:

FIG. 2 is a side view of one tine of the forceps of FIG. 1;

FIG. 3 is a top view of the tine of FIG. 2;

DETAILED DESCRIPTION OF THE INVENTION

Figure 1:
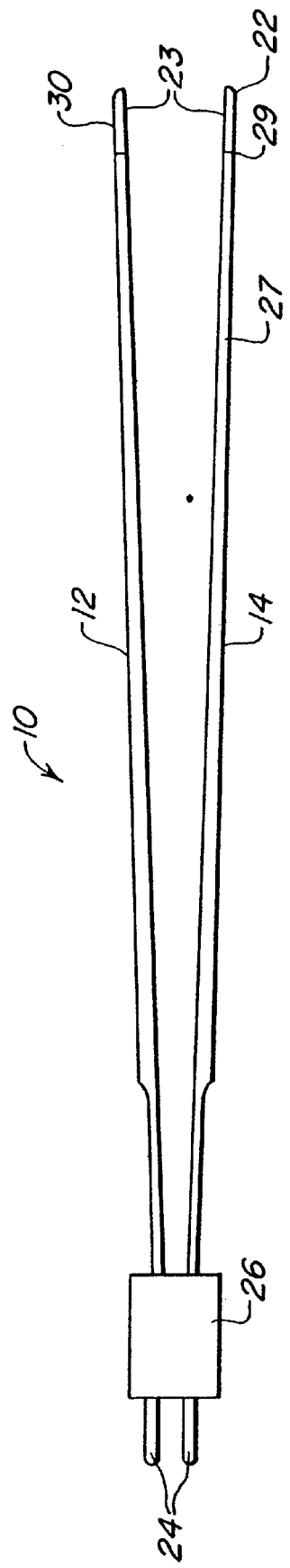
FIG. 1 is a side view of electro-surgical forceps according to the present invention.

Referring to FIGS. 1–3, a bipolar forceps 10 has first and second tines or electrode members 12 and 14. Each of the tines is elongated and extends from a first end 20 to a second end or tip 22. The tines are generally flat to have a greater width than depth, such that the tips are configured for gripping tissue between opposed surfaces 23. Forceps are generally provided in a range of tip widths, from 0.1 mm to 3 mm, to accommodate differently sized blood vessels. First ends 20 are electrically connected in any suitable manner, such as by crimping, welding, or soldering, to terminal pins 24. First ends 20 along with the terminal pins 24 are encapsulated using an epoxy based material or otherwise mounted within an insulating cap portion 25. Holes 28 stamped near the end 20 allow epoxy or other appropriate potting material to flow through and around the tines to fix the tines more firmly within the cap portion. If desired, the tines may be insulated with an insulating material 27 along most of their length from the cap portion 26 to a location 29 close to the tips. Serrated finger grips 31 may be formed in each tine to aid the physician in gripping the forceps during use.

Figure 4:
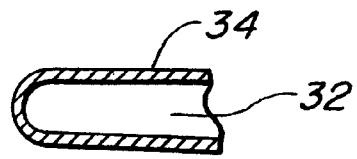
FIG. 4 is a cross sectional view along line IV—IV in FIG. 3.
Figure 5:
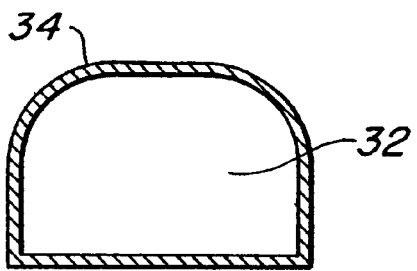
FIG. 5 is a cross sectional view along line V—V in FIG. 3.
Figure 6:
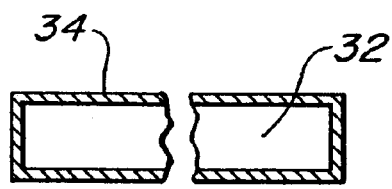
FIG. 6 is a cross sectional view along line VI—VI in FIG. 3.
Figure 7:
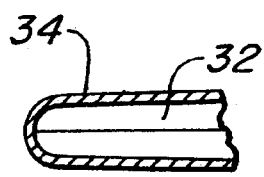
FIG. 7 is a cross sectional view along line IV—IV in FIG. 3 illustrating a bi-laminate core.

Referring more particularly to FIGS. 4–6, at least one and preferably both of the tines comprise a multi-layered structure along the entire length. The inner layer or core 32 is formed of a metal such as stainless steel, nickel, or titanium. The core may also have a bi-laminate (FIG. 7) or a tri-laminate structure of several metal layers, one of which may also include copper.

The core of the tine is covered by an outer plating 34. All or substantially all of the tine is covered by the plating, from the first end 20 to the tip 22. The plating material has a higher thermal conductivity than the core. A higher thermal conductivity enables the forceps tips to cool down more quickly when the power to the forceps is turned off. Preferably the plating material also has a higher electrical conductivity than the core. A higher electrical conductivity enables coagulation of the tissue to occur more quickly with less impedance. By specifying that substantially all of the tine is plated, it will be understood that insignificantly small portions of the tine may remain unplated or incompletely plated, as long as the resulting forceps performs during coagulation as though all of the tine is plated, as described further herein, as would be understood by one of skill in the art.

Suitable plating materials are rhodium, gold, silver, aluminum, palladium, tungsten, and nickel. The plating thickness should be at least 0.001 inch, and preferably at least 0.004 inch. A plating thickness of greater than 0.010 inch does not yield results sufficiently superior to warrant use of additional plating material. In particular, a range of 0.004 inch to 0.008 inch has been found to give good thermal conductivity and coagulation performance while providing suitable wear resistance at the tips.

Samples of stainless steel forceps were manufactured according to the present invention with silver plating in various thicknesses and were tested to determine their ability to coagulate tissue without sticking to the tissue. The plating thickness ranged from approximately 0.002 inch to 0.012 inch. Beef liver was used as a test medium to simulate clinical tissue. The forceps were connected, one at a time, to a standard electrosurgical generator using a standard bipolar cord. Each forceps was used to coagulate the beef liver tissue at various generator output settings and a subjective determination of the sticking of the coagulated tissue to the tine was made after each use. The performance of forceps of the invention was also compared with standard highly polished stainless steel forceps with no plating.

The silver-plated forceps of the present invention having a plating thickness of greater than 0.004 inch were consistently able to coagulate tissue without tissue adhering to the tines. The silver-plated forceps of the present invention having a plating thickness of less than 0.004 inch performed substantially similarly to the standard stainless steel forceps, with some sticking of tissue occurring.

Because the entire tine of the forceps of the present invention is plated, the thickness of the plating can be less than 0.010 inch and still achieve good performance. By comparison, in prior art forceps in which the tip alone is plated, the plating thickness must be greater than 0.010 inch to achieve good performance. Plating of the entire tine uses more material than plating only the tip. However, the resulting forceps perform more consistently in the coagulation of tissue than forceps plated solely at the tip.

The forceps 10 of the present invention are manufactured by beginning with stainless steel stock for the core that is cleaned and cut into strips. The strips are cut to the appropriate length for a tine 12 or 14. A taper is stamped at one end of the strip for the tip of the tine. Serrations for the finger grip 31 are stamped into a mid portion of the strip. The rear or spring section 42 is cold formed, as by rolling, to compress its thickness and to work harden the material. Work hardening of the material in this section strengthens the material, enabling a physician to squeeze the tines together repeatedly to grasp tissue and release the tines to return to their rest position. The perimeter 44 of the strip is stamped to form the general shape of the tine. Depending on the particular application, the tine could have a generally straight configuration or could have bends along its length, as illustrated in FIG. 3. The perimeter of the tine is formed, as by a coining process to form the edges. A tab 40 is stamped, deburred, and formed at the first end 20 of the tine. The terminal pins 24 are attached to the tabs in any suitable manner, such as by crimping, welding, or soldering.

Figure 8:
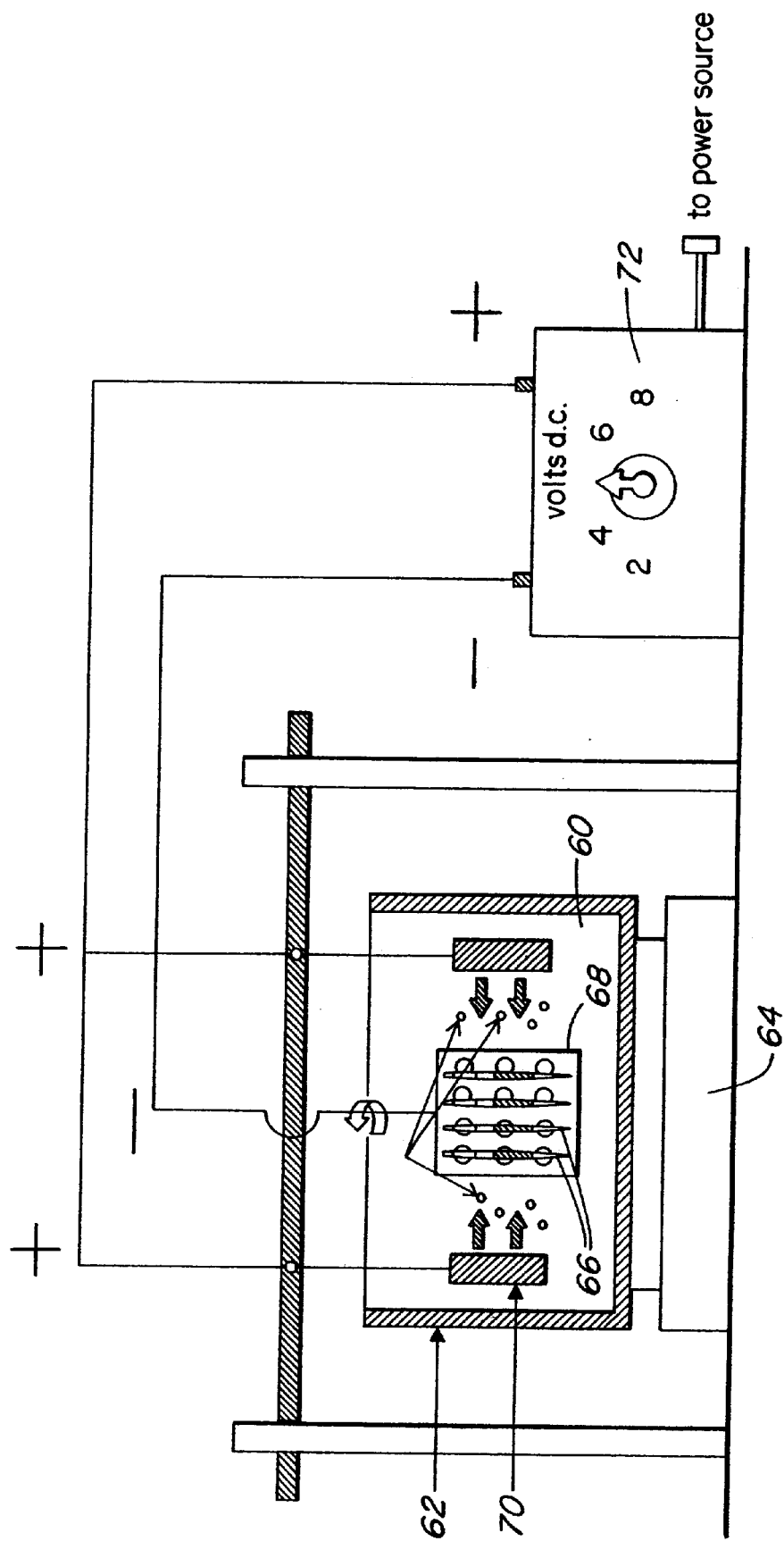
FIG. 8 is a schematic illustration of an electroplating process for forming forceps according to the present invention.

A batch of tines is then plated. See FIG. 8. An electroplating process is preferred to ensure that each tine is plated from the first end 20 to the tip 22 with a uniform coating. Electroplating is the deposit of a very thin layer of metal electrolytically onto a base metal to enhance or change its appearance or properties. A liquid solution 60 known as an electrolyte is placed in a bath tank 62. The plating bath solution 60 includes the desired plating metal dissolved as positively charged ions suspended in solution. For example, for a silver plating, a silver electrolyte is provided, which is generally silver cyanide, potassium cyanide and potassium carbonate with a silver concentration generally between 5 and 40 g/l. The plating bath solution is a conductive medium when a low DC voltage is applied to the bath.

Tines 66 to be plated are placed in a perforated container or barrel 68 or on a rack (not shown) that is lowered into the bath. The tines are in contact with the barrel or rack for electrical communication therewith. The terminal pins are masked to prevent them from being plated. If the pins were plated, they would become too thick. The barrel or rack holding the tines is located generally in the center of the plating bath and, with the tines, acts as a negatively charged cathode. The barrel may be suspended for rotation or placed on rollers within the bath. The tines within the barrel are loose and are gently agitated by the rotation or rolling of the barrel, which aids in achieving an even coating. If a rack is used, the tines are hung on the rack using C-shaped copper wire clips through the holes in the tines and through holes in the rack. The rack is reciprocated back and forth approximately two inches to agitate the bath to achieve a more even distribution of the metal plating. The bath solution may also be agitated in any other suitable manner to provide more uniform plating of the tines.

Positively charged anodes 70 to complete the DC circuit are positioned at the edges of the plating tank 62. The anodes are in contact with the bath solution and are positioned so that they do not restrict the current density. Preferably, the anodes are formed with a surface area equal to or greater than the cathode area of the tines (the total surface area to be plated). Also, the anodes are preferably formed of the plating metal, for example, silver, to replenish the plating metal in the bath during the process. Alternatively, additional plating metal may be added as the process depletes the metal in solution. Any suitable number and/or size of anodes are provided to ensure sufficient anode surface area to achieve a suitable plating speed. Generally, the greater the anode surface area is, the greater the current density and plating speed are.

A rectifier 72 in electrical communication with the anodes and the cathodes converts AC power to the desired carefully regulated low voltage DC current. Standard silver plating is generally performed with a current density ranging between 5 and 15 A/ft$^2$. Higher plating rates may be achieved at greater current densities, for example, 25 to 100 A/ft$^2$.

The bath may be heated by a heater 64 to increase the plating rate, although this is not necessary. Standard silver plating is suitably performed at 60 to 80° F. Higher plating rates may be achieved at increased temperatures, such as 105 to 158° F. In a standard plating system, the plating rate is approximately 0.0024 in/hr. To achieve a preferred thickness for the present invention at this rate, the plating process generally takes somewhat longer than two hours.

Other plating processes can be used, such as chemical vapor deposition (CVD), physical vapor deposition (PVD), or thermal spraying. In CVD, a volatile chemical compound of the coating material is evaporated in combination with a gas, and the condensate is deposited onto the article to be coated. This method is generally used when there is no other feasible way of depositing the desired coating material onto the substrate. CVD may also be used to achieve a compound coating material in a single coating process.

In PVD, the coating element is evaporated and deposited as a condensate onto the article to be coated. The deposition process may be enhanced by passing the vaporized atoms through an electric field, known as sputtering. The atoms may also be focused directly onto the substrate using an ion beam. The article to be coated may be bombarded with ions before or during the deposition of the coating. The ion bombardment aids in the removal of surface contaminants and/or the adherence of the coating material on the substrate.

Thermal or hot spraying methods are processes in which the coating material is melted, atomized, and then sprayed onto the surface to be coated in a stream of compressed air or other gas. Thermal spraying methods are some of the more simple coating methods.

After the tines have been plated, a pair of tines is encapsulated in insulating material 27, if desired, and affixed within the cap portion 25. The insulation 27, if present, is, for example, a plastic material capable of withstanding the high temperatures generated during use. The insulation may be formed in any suitable manner, such as by spraying on a liquid that dries to form a solid coating. The tips of the tines are left uninsulated for a suitable distance, such as ⅜ inch. The insulation is typically 0.010 to 0.05 inch thick.

The invention is not to be limited by what has been particularly shown and described, except as indicated by the appended claims.

What is claimed is:

1. An electro-surgical forceps comprising:
   an insulated cap portion;
   at least one terminal extending from and fixed to the cap portion; and
   a pair of tines, each tine being generally elongated and having a tip and an opposite end fixed within the cap portion, at least one of the pair of tines electrically connected to the at least one terminal within the cap portion and further comprising:
   a core comprising a metal layer formed of stainless steel, nickel or titanium, and
   an outer plating covering the core, comprising a material having a thermal conductivity or an electrical conductivity greater than the core, and
   wherein the outer plating covers substantially all of the core from the tip to the opposite end.

2. The forceps of claim 1, wherein the material of the outer plating comprises silver.

3. The forceps of claim 1, wherein the material of the outer plating comprises a commercially pure metal, the metal comprising rhodium, gold, silver, aluminum, palladium, tungsten, or nickel.

4. The forceps of claim 1, wherein the outer plating has a thickness of at least 0.001 inch.

5. The forceps of claim 1, wherein the outer plating has a thickness of less than 0.010 inch.

6. The forceps of claim 1, wherein the outer plating has a thickness ranging from 0.001 inch to 0.010 inch.

7. The forceps of claim 1, wherein the outer plating has a thickness of at least 0.004 inch.

8. The forceps of claim 1, wherein the core further includes a second layer, the second layer formed of stainless steel, nickel, titanium, or copper.

9. The forceps of claim 8, wherein the core further includes a third layer, the third layer formed of stainless steel, nickel, titanium, or copper.

10. The forceps of claim 1, further comprising an insulating coating over the tine extending from the cap portion to a location near the tip.

11. A method of forming the electro-surgical forceps of claim 1, comprising:
    forming a strip of metal into the pair of tines;
    plating the at least one tine with the outer plating to cover the entire surface of the at least one tine; and
    mounting the pair of tines and the at least one terminal to the insulated cap portion.

12. The method of claim 11, wherein the plating step comprises electroplating the at least one tine.

13. The method of claim 11, wherein the electroplating step comprises disposing the at least one tine in an electrolyte solution and applying a current between an anode and the strip, the strip comprising a cathode.

14. The method of claim 11, wherein the at least one terminal is attached to the at least one tine prior to the plating step, and the at least one terminal is masked during the plating step.

* * * * *